US00PP35296P2

(12) United States Plant Patent
Phillips

(10) Patent No.: US PP35,296 P2
(45) Date of Patent: Aug. 8, 2023

(54) ***ACTINIDIA* PLANT NAMED 'Y19'**

(50) Latin Name: *Actinidia chinensis*
Varietal Denomination: Y19

(71) Applicant: Douglas A. Phillips, Visalia, CA (US)

(72) Inventor: Douglas A. Phillips, Visalia, CA (US)

( * ) Notice: Subject to any disclaimer, the term of this patent is extended or adjusted under 35 U.S.C. 154(b) by 0 days.

(21) Appl. No.: 17/980,899

(22) Filed: Nov. 4, 2022

(51) Int. Cl.
*A01H 5/08* (2018.01)
*A01H 6/00* (2018.01)

(52) U.S. Cl.
USPC ..... Plt./156

(58) Field of Classification Search
USPC ..... Plt./156
CPC ..... A01H 5/08; A01H 5/00; A01H 6/00
See application file for complete search history.

(56) References Cited

U.S. PATENT DOCUMENTS

PP11,066 P * 9/1999 Lowe ..... Plt./156

* cited by examiner

*Primary Examiner* — June Hwu
(74) *Attorney, Agent, or Firm* — Cooley LLP

(57) ABSTRACT

The present disclosure relates to a new and distinct *Actinidia chinensis* plant named 'Y19', characterized by a twining habit of medium to strong vigor, exceptional sweet fruit with a slightly tangy finish, and resistance to stylar end shrivel in hot climates.

9 Drawing Sheets

Genus and species: *Actinidia chinensis*.
Variety denomination: 'Y19'.

BACKGROUND ON THE NEW PLANT

The present disclosure comprises a new and distinct variety botanically known as *Actinidia chinensis*, and hereinafter referred to by the variety name 'Y19'.

The new *Actinidia* variety 'Y19' was selected from a population of seedlings derived from mature kiwi fruit of unknown parentage. The seedlings were planted in October of 2016 and germination occurred a few weeks later. Seedlings continued to grow in a greenhouse throughout 2017. Graft wood was taken from dormant plants in December of 2017 and grafted onto established two-year-old *Actinidia deliciosa* 'Bruno' rootstock. Each seedling was also planted near the corresponding grafted plant in Visalia, Calif. in December 2017. The new variety was selected from many grafted plants and seedlings in October of 2019. 'Y19' was found to reproduce true to type in successive generations of asexual propagation via grafting dormant buds from the original 2019 selection onto kiwifruit rootstocks, 'Bruno' and 'Bounty 71', in Visalia, Calif.

SUMMARY OF THE DISCLOSURE

The following are outstanding and distinguishing characteristics of this new variety when grown under normal horticultural practices in Visalia, Calif.

1. The length to width ratio of the fruit is greater than most other varieties;
2. Exceptionally sweet fruit with a slightly tangy finish; and
3. Resistance to stylar end shrivel.

BRIEF DESCRIPTION OF THE PHOTOGRAPHS

DESCRIPTION OF THE NEW VARIETY

Figure 1:
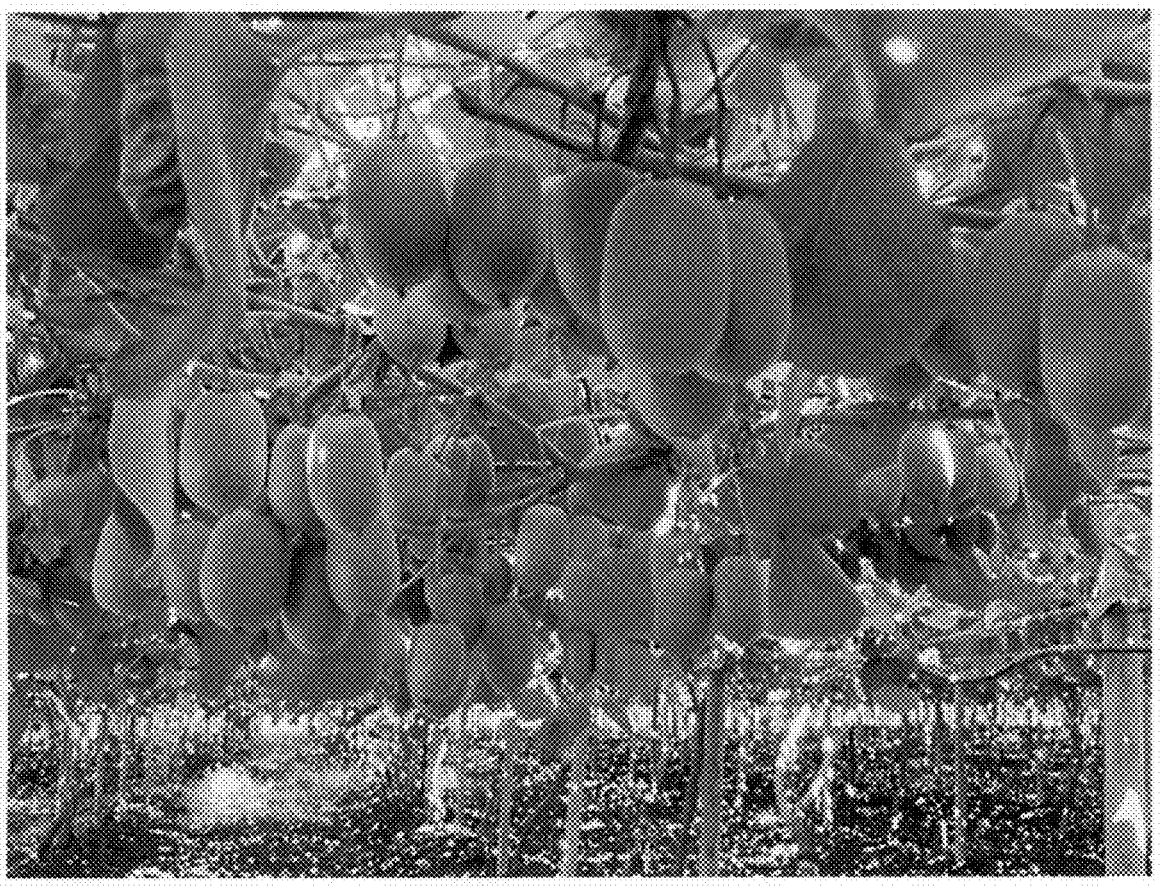
FIG. 1 shows typical fruit on the vine of the new kiwifruit variety 'Y19' of a plant grafted onto two-year old 'Bruno' rootstock in late December 2017. The photograph was taken in September 2022.
Figure 2:
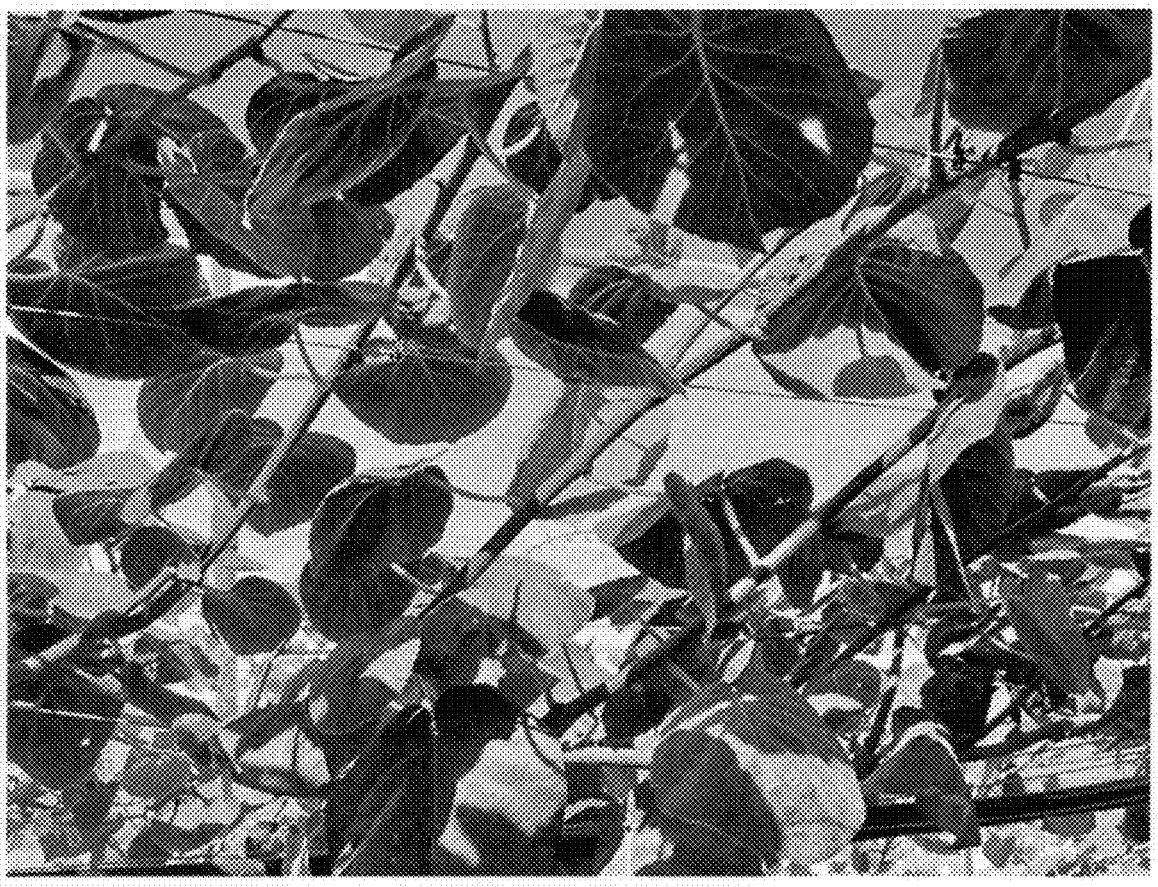
FIG. 2 shows typical mature lateral canes of 'Y19' that will produce fruit the following year. The plant was grafted in December 2021 onto two-year old 'Bruno' rootstock and the photograph was taken in October 2022.
Figure 3:
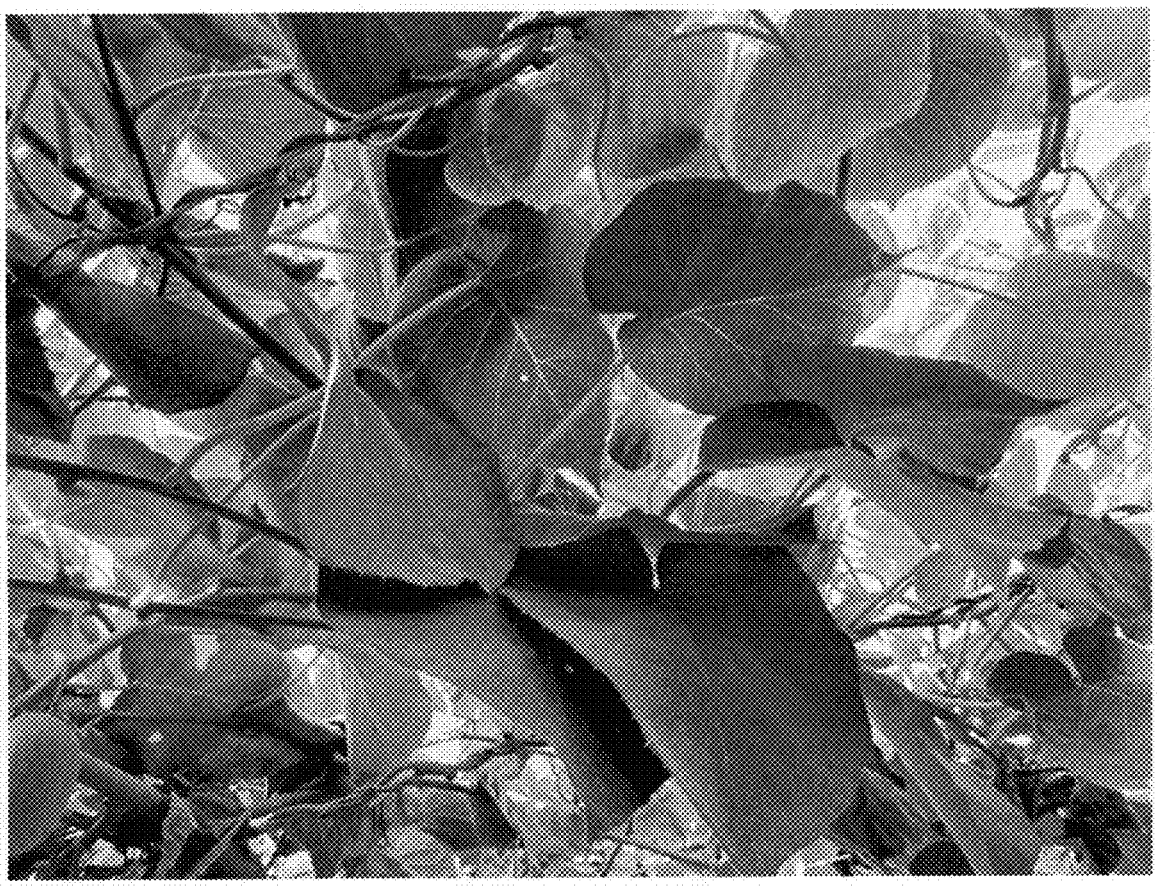
FIG. 3 shows mature leaves of the new kiwifruit variety 'Y19' of a plant grafted onto two-year old 'Bruno' rootstock in early January 2020. The photograph was taken in late September 2022.
Figure 4:
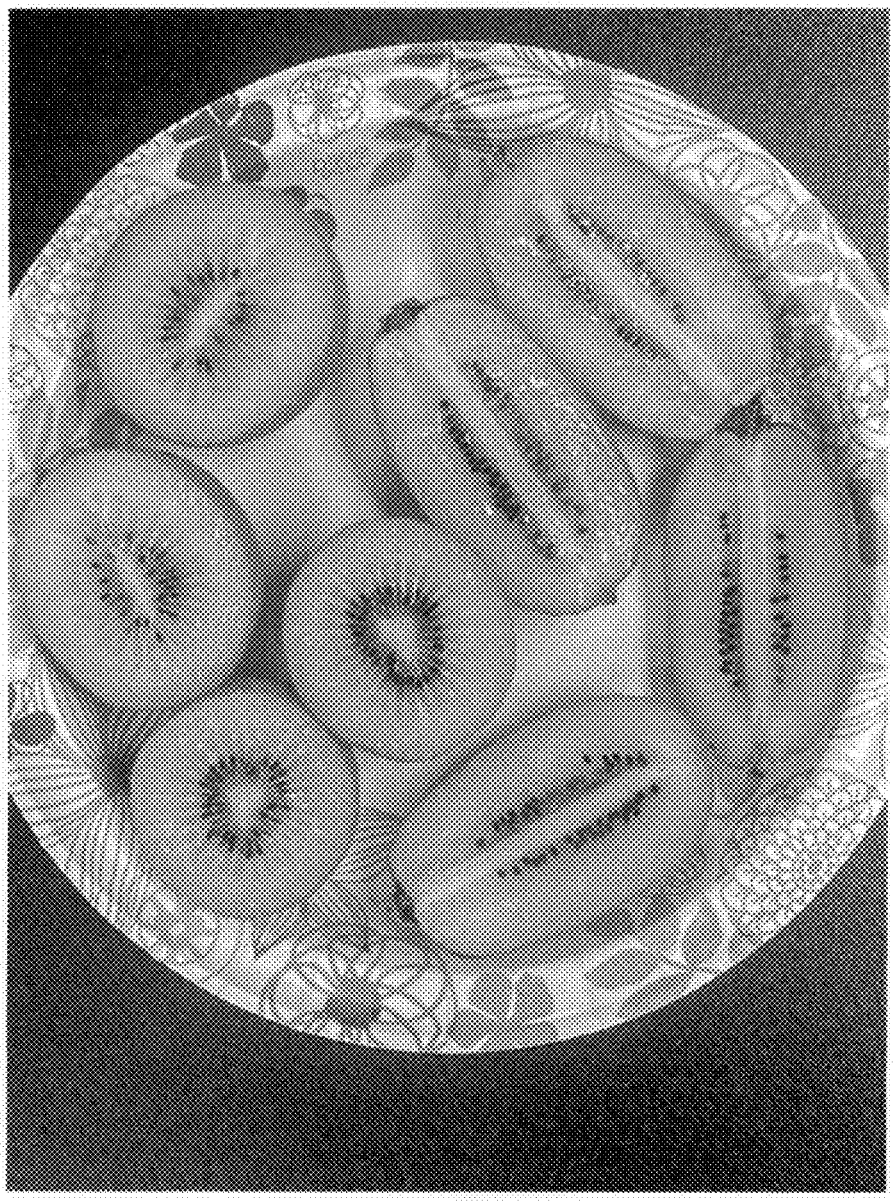
FIG. 4 shows typical fruit of the new variety 'Y19' in longitudinal-section and cross-section.
Figure 5:
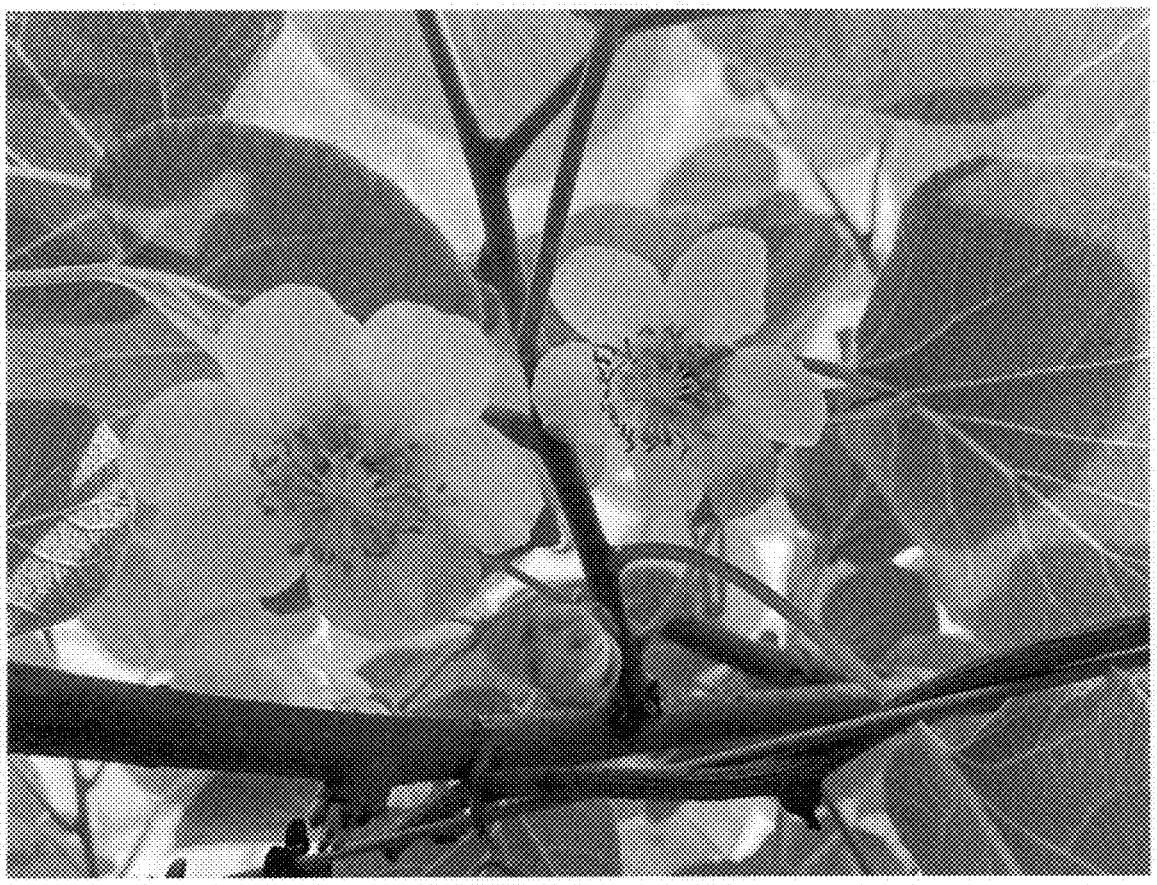
FIG. 5 shows the flowers of the new kiwifruit variety 'Y19' on the vine of a plant grafted onto two-year old 'Bruno' rootstock in early January 2020. The photograph was taken in April 2022.
Figure 6:
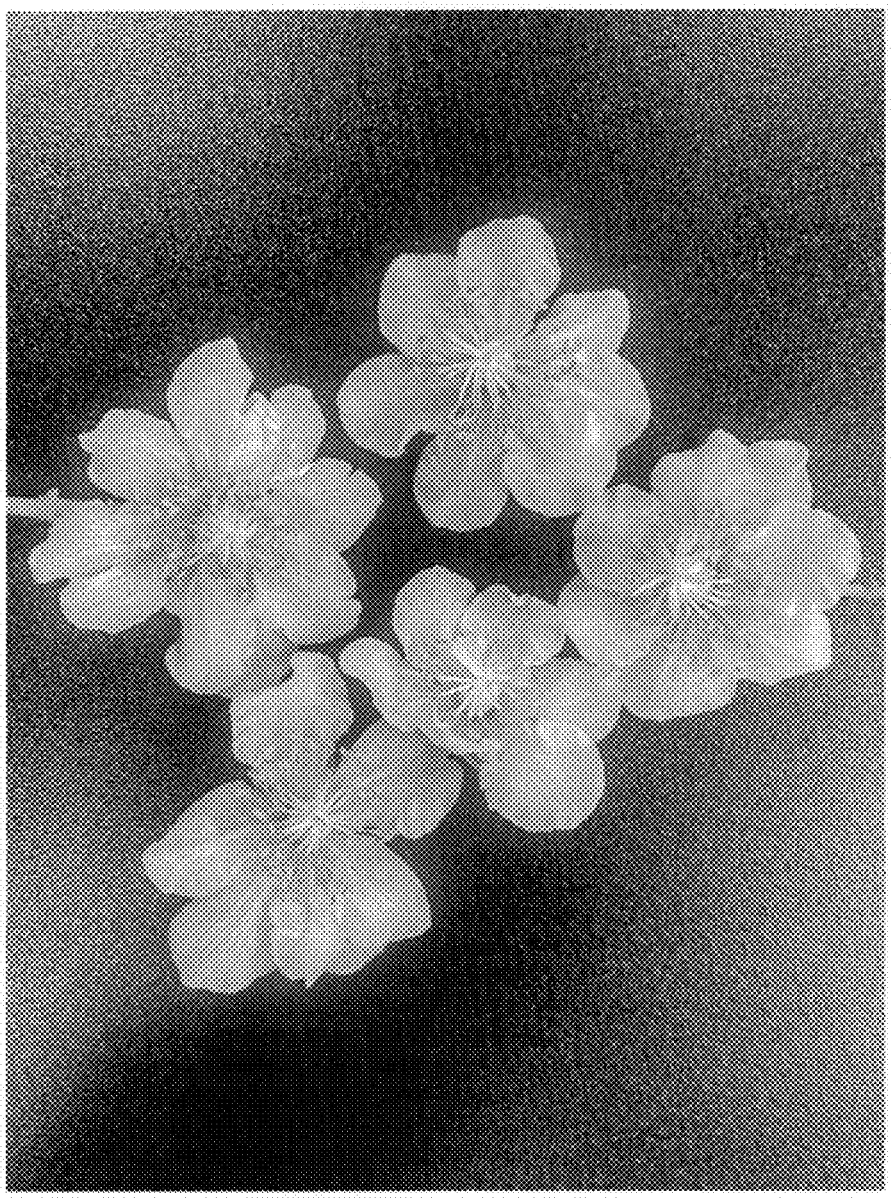
FIG. 6 shows the flowers of the new kiwifruit variety 'Y19'.
Figure 7:
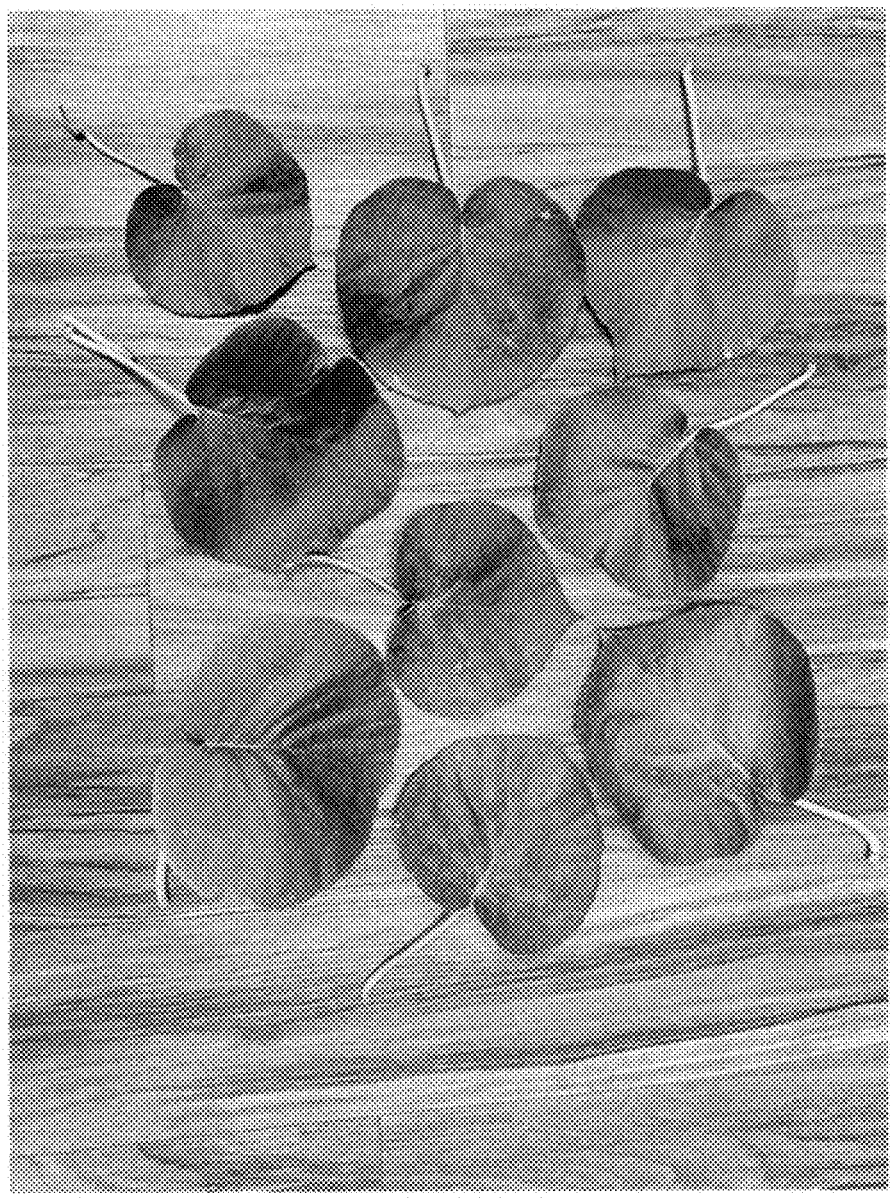
FIG. 7 shows mature leaves from above (adaxial surface) of the new variety 'Y19'.
Figure 8:
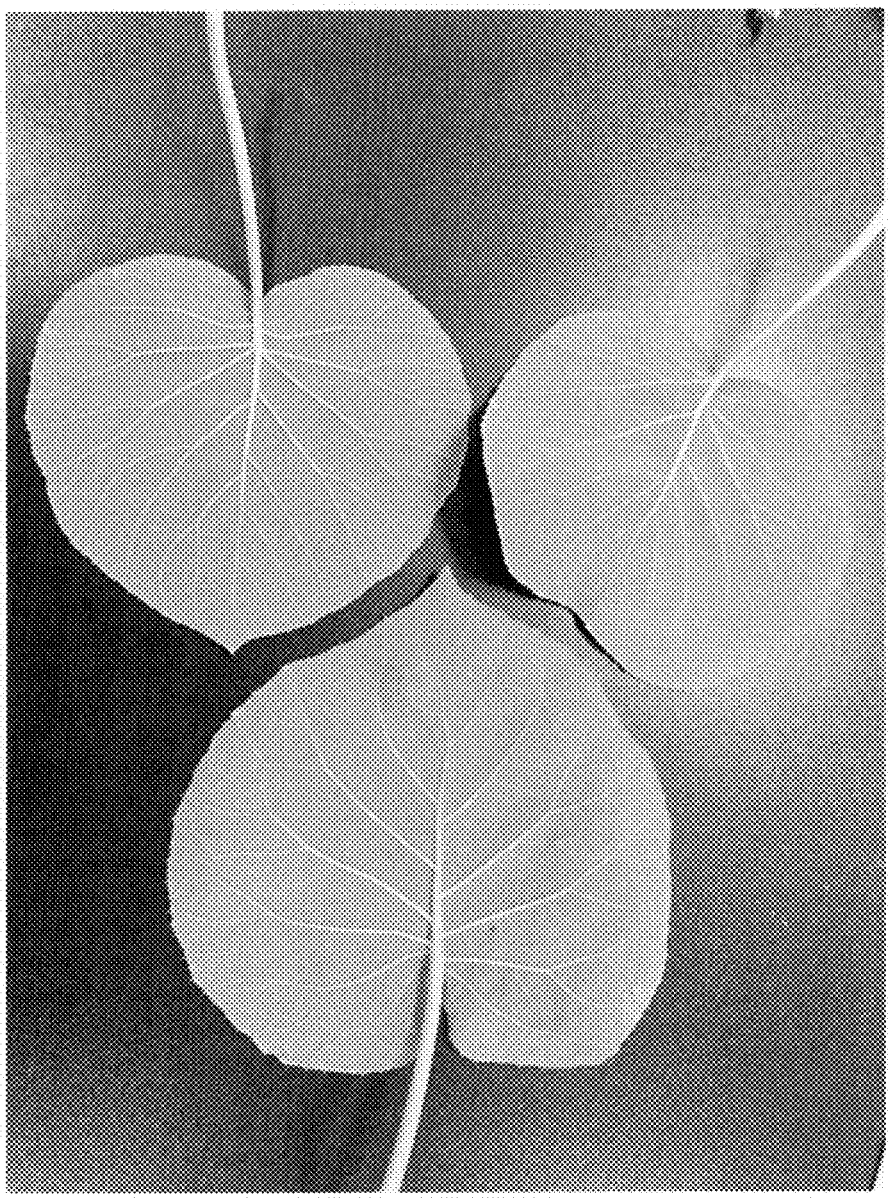
FIG. 8 shows mature leaves from below (abaxial surface) of the new variety 'Y19'.
Figure 9:
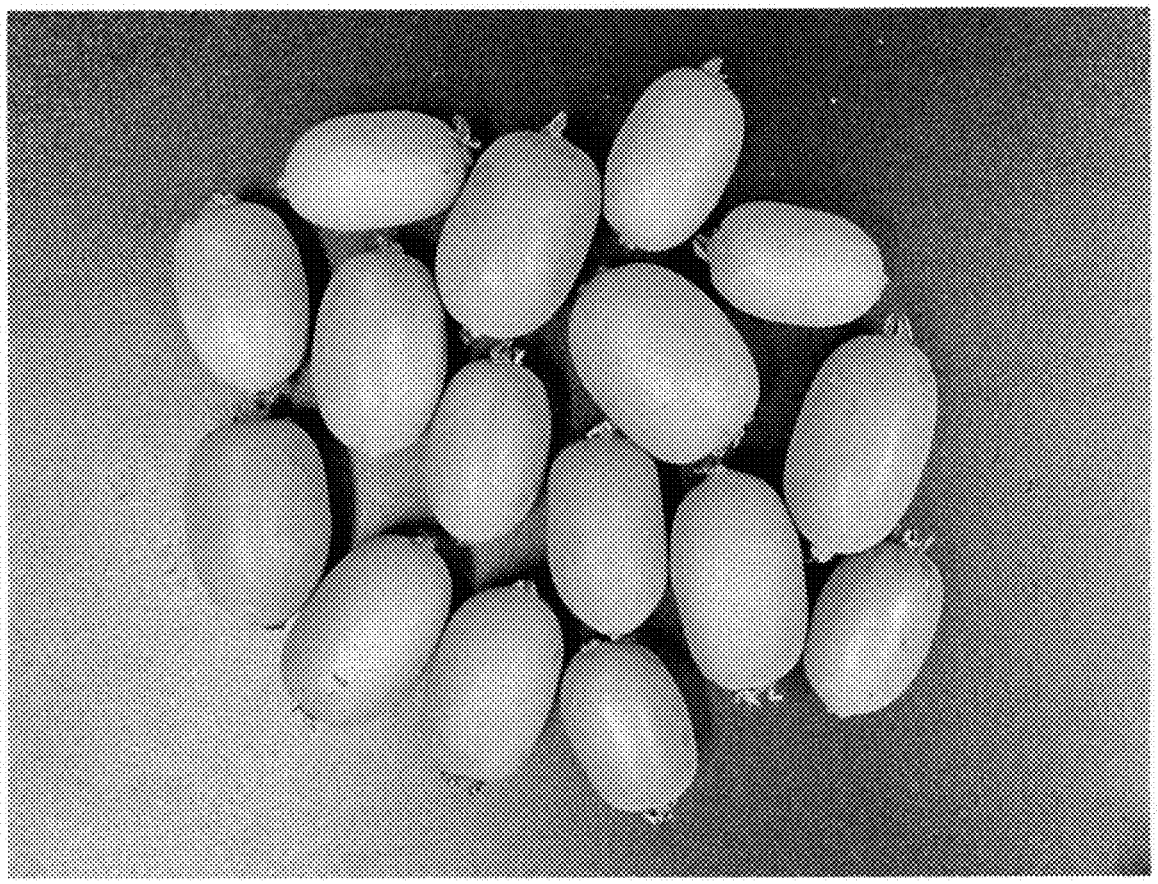
FIG. 9 shows typical fruit of the new variety 'Y19'.

The following detailed descriptions set forth the distinctive characteristics of 'Y19'. The data which define these characteristics were collected near Visalia, Calif. in the Autumn of 2021 through the Autumn of 2022. Data was collected on the original 2019 selection as well as the mother plant and vines grafted onto existing *A. deliciosa* 'Bruno' and *A. macrospermum* 'Bounty 71' rootstock in 2021. Plants were managed under standard orchard practices for this region of California. The plants were grown on a standard pergola trellis at a height of 1.95 meters, and each plant was allowed to fill a canopy area of approximately 15.6 $m^2$. The plants were in their $3^{rd}$ and $5^{th}$ leaf from grafting and were considered mature. Measurements from 9 plants were taken to describe each characteristic. Horticultural terminology is used in accordance with UPOV guidelines for kiwifruit. Color references are to The R.H.S. Colour Chart of The Royal Horticultural Society of London (R.H.S.) sixth edition (2019 reprint).

Classification:

*Family*.—Actinidiaceae.

*Botanical*.—*Actinidia chinensis*.

*Common name*.—Kiwifruit.

*Denomination*.—'Y19'.

Parentage: Unknown.

Plant:

*Age of the plants described*.—Between 1 year and 4 months from grafting to 4 years and 10 months old.

*Sex expression*.—Female.

*Ploidy*.—Tetraploid.

*Average height*.—1.95 meters.

*Average width*.—4.5 meters.

*Plant vigor*.—Medium.

*Young shoot color* (*R.H.S.*).—Yellow green 145B.

*Young shoot texture*.—Smooth with very fine tomentose hairs.

*Young shoot density of hairs*.—Low density.

*Young shoot anthocyanin coloration of growing tip*.—Absent or very weak.

*Mature branch/shoot diameter*.—Thick, averaging 1.4 cm between bud 5 and 6.

*Mature branch/shoot length*.—Variable, averaging 200 cm.

*Mature branch/shoot texture*.—Smooth.

*Mature branch/shoot color* (*R.H.S.*).—Light yellowish brown 199C to moderate olive brown 199A with more sun exposure.

*Stem lenticels description*.—Length: Average 1.5 mm. Width: Average 0.9 mm. Color (R.H.S.): 165B. Appearance and shape: Raised and elliptical. Quantity: Moderate.

*Stem prominence of bud support*.—Weak.

*Stem presence of bud cover*.—Absent.

*Stem size of hole in bud cover*.—Medium.

*Stem pith*.—Lamellate.

*Stem leaf scar*.—Moderately depressed.

*Trunk diameter*.—6 cm to 8 cm when measured at 15 cm to 25 cm from the ground.

*Trunk texture*.—Slightly rough.

*Trunk color* (*R.H.S.*).—Light brownish grey N200C.

Leaf:

*Average length*.—15 cm with range from 10 cm to 20 cm.

*Average width*.—18 cm with range from 12 cm to 22 cm.

*Shape of blade*.—Cordate.

*Apex*.—Cuspidate.

*Base*.—Cordate with mostly basal lobes slightly apart.

*Margin*.—Slightly ciliate.

*Texture of upper* (*adaxial*) surface.—Moderately rough.

*Texture of lower* (*abaxial*) surface.—Non-pubescent.

*Color* (*R.H.S.*).—Mature foliage upper surface: Greyish olive green NN137B. Mature foliage lower surface: Moderate yellowish green 147B. Immature foliage upper surface: Moderate yellowish green N138A. Immature foliage lower surface: Moderate yellowish green N138C.

*Petiole*.—Length (cm): Averages 12 cm with range from 8 cm to 16 cm. Pubescence: Absent. Anthocyanin coloration of upper side: Weak. Color (R.H.S.): Moderate red 181B on upper side.

Flower:

*Type*.—Solitary.

*Number of inflorescences per fruiting shoot*.—1 to 8, with an average of 4.7.

*Number of flowers per inflorescence*.—1 to 3; a single king flower that produces the largest fruit and 1-2 side flowers that produce smaller fruit, if not removed as buds.

*Flower shape*.—Hemispherical.

*Flower bud position of first spike*.—High.

*Bud color* (*R.H.S.*).—Brownish orange 164A.

*Bud shape*.—Oblong.

*Bud break*.—Medium, about March 9$^{th}$ to March 14$^{th}$ in Visalia, Calif.

*Date of first flower*.—April 5$^{th}$ to April 11$^{th}$ in Visalia, Calif.

*Diameter*.—Average 6.5 cm.

*Depth*.—Average 3.7 cm.

*Pedicel length at full bloom*.—3.5 cm.

*Petal quantity*.—5 to 9, average 6.8.

*Petals overlapping*.—Yes.

*Petals*.—Length: Approximately 2.5 cm. Width: Approximately 2.4 cm. Shape: Spatulate. Aspect: Slightly undulating. Margin: Entire. Texture (both upper and lower surfaces): Glabrous. Base: Attenuate. Apex: Obtuse. Color, upper surface (R.H.S.): White NN155D to Pale yellow 158B, when fully open. Color, lower Surface (R.H.S.): Yellow green 146C on base with the remaining petal lower surface pale yellow 158B at full bloom.

*Filament color* (*R.H.S.*): White NN 155C.

*Stamen quantity*.—50 to 62 with an average of 56.

*Anther color* (*R.H.S.*).—Vivid yellow 15B.

*Attitude of styles*.—Semi-erect.

*Style color* (*R.H.S.*).—Yellowish white 155D.

*Style length*.—6 mm.

*Style quantity*.—Between 26 and 36 with an average of 30.

*Hair on ovary*.—Dense.

*Color of ovary* (*R.H.S.*).—Yellowish white 155D.

*Ovary shape and length*.—Ovoid, approximately 0.8 cm.

*Sepals*.—Quantity: 6 to 7, average 6.8. Color (R.H.S.): Yellow green 143C. Width: Approximately 0.5 cm. Length: Approximately 0.8 cm. Texture: Smooth. Shape: Deltate. Margin: Entire. Apex: Acute. Base: Truncate. Calyx ring: Present, 2 mm wide.

*Peduncle*.—Length: Average 3.5 cm. Diameter: Average 0.2 cm. Color (R.H.S.): Yellow green 144C. Texture: Smooth.

Fruit:

*Average weight*.—118 grams when thinned to a crop load of 35 to 45 fruit per square meter of female canopy.

*Minimum weight*.—70 grams.

*Maximum weight*.—160 grams.

*Dry matter at harvest*.—Between 22% and 24% of the undried or wet sample.

*Average length*.—7.2 cm.

*Average diameter*.—4.15 cm.

*Color outer pericarp* (*R.H.S.*).—Light greenish yellow 8C.

*Color inner pericarp* (*R.H.S.*).—Light greenish yellow 8B.

*Core color* (*R.H.S.*).—Yellowish white 155B.

*Core diameter*.—0.6 cm average.

*General shape*.—Oblong.

*Brix at consumption*.—18 to 21.

*Brix at harvest*.—10 to 14.

*Fruit acidity*.—Slightly acidic.

*Fruit peduncle length*.—Average 60 mm.

*Fruit peduncle width*.—Average 4.5 mm.

*Median cross section shape*.—Circular.

*Stylar end shape*.—Slightly blunt protruding.

*Shoulder shape*.—Truncate.

*Calyx ring*.—Present.

*Calyx ring expression*.—Weak.

*Skin color at harvest* (*R.H.S.*).—Yellow green 148B when shaded and with sun exposure yellowish brown 199C.

*Hair on fruit skin*.—Present, slightly downy with very short hairs on mature fruit in low density.

*Hair adherence to skin*.—Weak.

*Hair color* (*R.H.S.*).—Brownish orange 165B.

*Skin adherence to flesh at maturity*.—Weak.

*Fruit core shape*.—Oblate.

*Core-woody spike*.—Minor.

*Lenticels on fruit*.—Present.

*Color of locules* (*R.H.S.*).—Light yellow 160B.

*Quantity of locules per fruit*.—Between 24 and 34 with an average of 28.

*Mature seed color* (*R.H.S.*).—Black 203D.

*Harvest time*.—October 1$^{st}$ to October 15$^{th}$, Visalia, Calif.

*Overall cropping quantity*.—Medium to heavy

*Fruit stem*.—Length. Average 4.2 cm. Diameter: Average 0.4 cm. Color (R.H.S.): Moderate brown 199C. Texture: Smooth.

Storage life of fruit: Shows potential for very long storability of 3 to 7 months at 0.5 to degrees Celsius while maintaining average flesh pressures of greater than 1 kgf.

Disease resistance or susceptibility: None observed.

Pest resistance or susceptibility: Dormant canes are susceptible to San Jose scale (*Quadraspidiotus perniciosus*). Leaves and fruit of 'Y19' are susceptible to Omniverous leafroller (*Platynota sultana*) after fruit set in the spring.

Temperature tolerance: Tolerates low temperatures to −4 degrees Celsius, when dormant and high temperatures to approximately 39 degrees Celsius without adverse effects. Less vulnerable to spring frost.

Water stress or drought tolerance: Shows slight tolerance to stress during hot summers. Resistant to stylar end shrivel.

Cultivation: 'Y19' plants have been grown on *A. deliciosa* 'Bruno' rootstock (unpatented), *A. macrospermum* 'Bounty 71' rootstock (not patented). Vegetative bud break occurs in early to mid-March near Visalia, Calif., with flowering starting in early to mid-April. More than 60% of the dormant winter buds produce shoots in the spring and more than 90% of these will produce flowers. 'Y19' vines start losing their leaves in December and, with adequate frosts, are largely defoliated by early to mid-January near Visalia, Calif.

COMPARISON WITH KNOWN VARIETY

'Y19' is a distinct variety of kiwi and is most similar to the kiwi commercial line 'Hort 16A' (U.S. Plant Pat. No. 11,066). The fruit of 'Y19' has a similar harvest date with 'Hort 16A'. However, 'Y19' produces more flowers than 'Hort 16A' and larger fruit than 'Hort 16A'. Total soluble solids measured in degrees brix, in ripe fruit ready for consumption, is higher in 'Y19' than in 'Hort 16A'. Additional differences between the two varieties are described in Table 1.

TABLE 1

Comparison with Similar Variety

| Characteristic | New variety: 'Y19' | Commercial line: 'Hort 16A' |
|---|---|---|
| Stylar end beak | Slight | Pronounced beak |
| Bud-break, harvest and full bloom | 10 to 14 days later than 'Hort 16A' | Very early bud-break and bloom |
| Stylar end shrivel | None observed | Prone to pre-harvest shrivel in hot climates |
| Vigor | Less vigorous than 'Hort 16A' | More vigorous than 'Y19' |
| Ploidy | Tetrapioid | Diploid |

'Y19' may also be compared to 'ZESY002' (U.S. Plant Pat. No. 22,355). The fruit shape of 'Y19' is more elongated and has a greater length to width ratio than 'ZESY002'. The stylar end of 'Y19' is blunt and has a slight protrusion compared to 'ZESY002' which is blunt with a slight indentation. Total soluble solids measured in degrees brix, in ripe fruit ready for consumption, is higher in 'Y19' than in 'ZESY002'.

What is claimed is:

1. A new and distinct cultivar of *Actinidia chinensis* plant named 'Y19' as herein illustrated and described.

* * * * *